US006800300B1

(12) United States Patent
Miller et al.

(10) Patent No.: US 6,800,300 B1
(45) Date of Patent: Oct. 5, 2004

(54) METHOD FOR TREATING AUTOIMMUNE AND ALLOIMMUNE DISEASES

(75) Inventors: Richard G. Miller, Toronto (CA); Brian Rabinovich, Toronto (CA)

(73) Assignee: Vasogen Ireland Limited, Shannon (IE)

( * ) Notice: Subject to any disclaimer, the term of this patent is extended or adjusted under 35 U.S.C. 154(b) by 0 days.

(21) Appl. No.: 09/541,033

(22) Filed: Mar. 31, 2000

(51) Int. Cl.$^7$ ................................................ A61K 35/14
(52) U.S. Cl. ...................... 424/529; 424/93.1; 424/93.7; 424/520; 424/810; 424/192.1; 424/278.1; 514/825; 514/885
(58) Field of Search ................................ 514/825, 885; 424/192.1, 184.1, 278.1, 93.1, 93.7, 520, 529, 810

(56) References Cited

U.S. PATENT DOCUMENTS

| | | | |
|---|---|---|---|
| 4,968,483 A | | 11/1990 | Müller et al. |
| 5,591,457 A | * | 1/1997 | Bolton |
| 5,605,690 A | * | 2/1997 | Jacobs et al. |
| 5,980,954 A | | 11/1999 | Bolton |

FOREIGN PATENT DOCUMENTS

WO    WO 98/07436    2/1998

OTHER PUBLICATIONS

Kim M. Murray et al., "Recombinant Human Tumor Necrosis Factor Receptor (p75) Fc Fusion Protein (TNFR:Fc) in Rheumatoid Arthritis", The Annals of Pharmacotherapy, Nov. 1977, vol. 31, pp. 1335–1338.
Marc Feldman et al., "Rheumatoid Arthritis", Cell, vol. 85, pp. 307–310, May 3, 1996.
Treatment Schedule for rhu TNFR:Fc (p50) for RA, phase II/III clinical trial (human).
Richard O. Williams et al., Successful therapy of collagen–induced arthritis with TNF receptor–IgG fusion protein and combination with anti–CD4, Immunology, 1995, vol. 84, pp. 433–439.
Paul H. Wooley et al., "Influence of a Recombinant Human Soluble Tumor Necrosis Factor Receptor FC Fusion Protein on Type II Collagen–Induced Arthritis in Mice", The Journal of immunology, vol. 151, pp. 6602–6607, No. 11, Dec. 1, 1993.

Genetic Engineering News, Companies Take Broad Range of Approaches to Develop Rheumatoid Arthritis Therapies, Jan. 15, 1997, vol. 17, No. 2., p. 1.
Chen, Y.L., et al., "Anti–tumor necrosis factor properties of non–peptide drugs in acute–phase responses," Eur. J. Pharmacol., Dec. 27, 1994, 271:(2–3), pp. 319–324. Abstract only.
Åkerlund, K. et al., (Jan. 1999) "Anti–Inflammatory Effects of a New Tumour Necrosis Factor–Alpha (TNF–α) Inhibitor (NCI–1493) in Collagen–Induced Arthritis (CIA) in Rats," Clin & Exp. Immunol. 115(1):32–41.
Morrow, J.K. (Jan. 15, 1997) "Companies Take Broad Range of Approaches to Develop Rheumatoid Arthritis Therapies," Genetics Engineering News vol. 17, No. 2, pp. 1, 7, 26.
Pearson, C.M. (1956) "Development of Arthritis, Periarthritis and Periostitis in Rats Given Adjuvants," Proc. Soc. Exp. Biol. Med. 91(1):95–101.
Ross, S. E. et al., (Dec. 15, 1997) "Suppression of TNF–α Expression, Inhibition of Th1 Activity, and Amelioration of Collagen–Induced Arthritis by Rolipram," J. Immunol. 159(12):6253–6259.
Terato, K. and REife, R. A. (May 7, 2002) "A Novel Model of Arthritis Induced With Monoclonal Antibodies to Type II Collagen," Stratagene Internet Website located at <http://www.stratagene.com/vol11_2/p56–57.htm> visited on May 7, 2002, 3 pages.

* cited by examiner

Primary Examiner—Patrick J. Nolan
(74) Attorney, Agent, or Firm—Foley & Lardner LLP

(57) ABSTRACT

Disclosed is a method for treating a mammalian subject suffering from an autoimmune or alloimmune disease by administering to the subject a drug treatment which results in at least partial remission of one or more symptoms of the autoimmune or alloimmune disease, and administering to the subject autologous mammalian blood which has been modified extracorporeally by exposure to at least one stressor selected from an oxidative environment, an electromagnetic emission and a temperature above or below body temperature. The modified mammalian blood is administered to the subject in an amount which is sufficient to maintain the remission of the symptoms of the autoimmune or alloimmune disease.

9 Claims, 1 Drawing Sheet

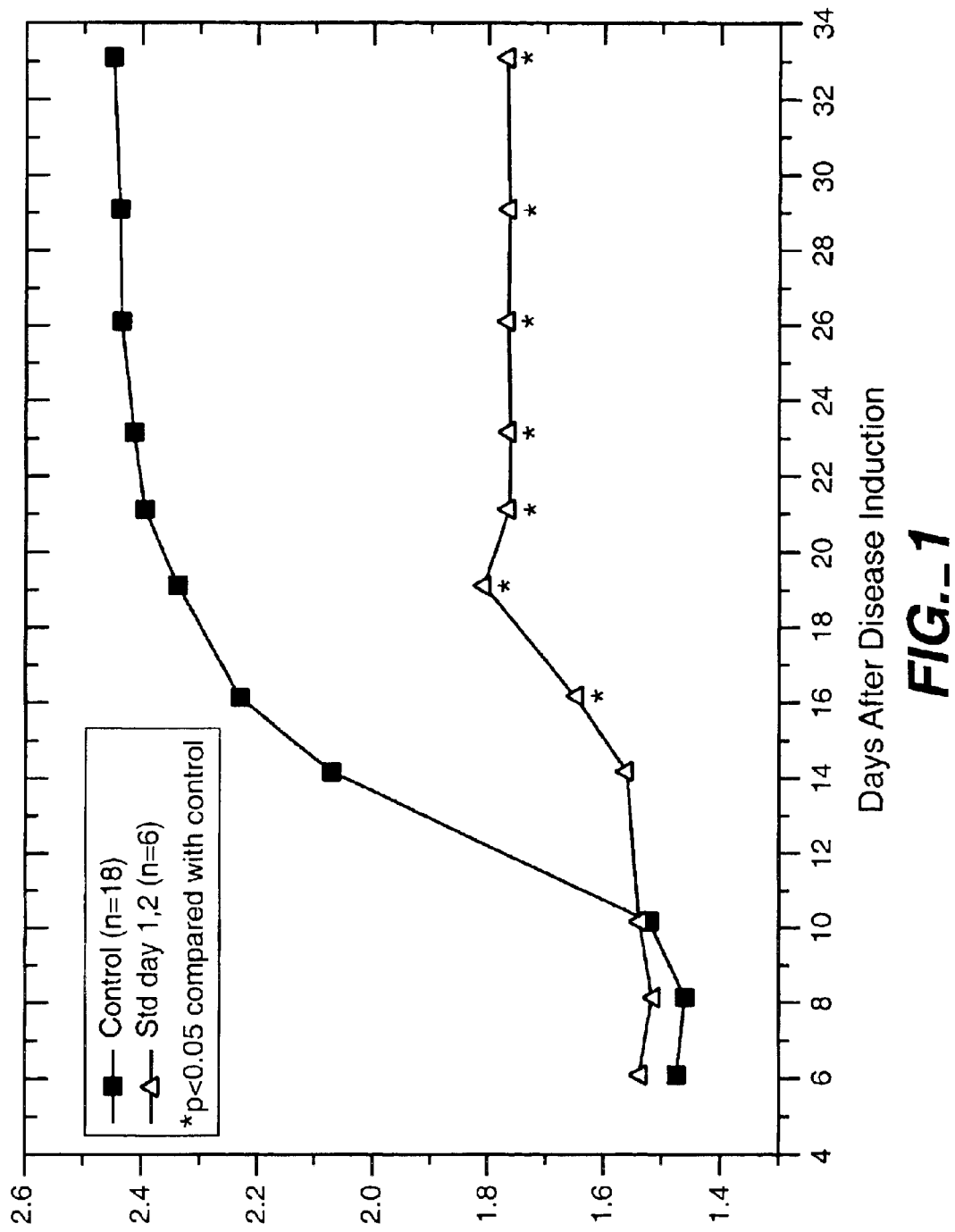
FIG._1

METHOD FOR TREATING AUTOIMMUNE AND ALLOIMMUNE DISEASES

CROSS REFERENCE TO RELATED APPLICATIONS

This application claims the benefit of U.S. Provisional Application Ser. No. 60/127,621, filed on Apr. 1, 1999.

FIELD OF THE INVENTION

This invention relates to medical treatments for autoimmune and alloimmune diseases, and more specifically to treatments comprising two components: a first component comprising a treatment which brings about a remission of a particular autoimmune or alloimmune disease and/or one or more symptoms associated with the disease; and a second component comprising administration of modified mammalian blood to effectively maintain remission of the disease and/or its symptoms.

BACKGROUND OF THE INVENTION

Autoimmune diseases are generally believed to be caused by the failure of the immune system to discriminate between antigens of foreign invading organisms (non-self) and tissues native to its own body (self). When this failure to discriminate between self and non-self occurs and the immune system reacts against self antigens, an autoimmune disorder may arise. Autoimmune diseases, or diseases having an autommune component, include rheumatoid arthritis, multiple sclerosis, systemic lupus erythromatosis (SLE), scleroderma, diabetes, inflammatory bowel disease, psoriasis and atherosclerosis. "Alloimmune diseases" are referred to herein as disorders such as graft versus host disease and tissue transplant rejection, in which an immune response against or by foreign, transplanted tissue can lead to serious complications or be fatal. In the treatment of these disorders, it is desired to prevent the body from reacting against non-self antigens.

While treatments are available which alleviate and bring about remission of autoimmune and alloimmune diseases and/or the symptoms associated with these diseases, many of these treatments do not treat the underlying cause of the disease and therefore must be continued indefinitely in order to maintain their beneficial effect.

Rheumatoid arthritis is an example of a common human autoimmune disease, affecting about 1% of the population. This disease is characterized by chronic inflammation of the synovial joints which may lead to progressive destruction of cartilage and bone.

Although there is no known cure for rheumatoid arthritis, a variety of drug treatments are currently available to alleviate symptoms of the disease and to slow the permanent and irreversible joint degradation associated with the disease. For example, treatment with non-steroidal anti-inflammatory drugs (NSAIDS) or glucocorticoids may provide relief of joint pain and swelling; disease-modifying anti-rheumatic drugs (DMARDS) such as hydroxychloroquine, methotrexate, sulfasalazine, D-penicillamine, gold (chrysotherapy) and azathioprine may be combined with NSAIDS and/or glucocorticoids to delay disease progression; and cyclosporines may be used to treat patients who do not respond to other therapies. Also known are type IV phosphodiesterase inhibitors, some of which have been shown to down-regulate the production of tumor necrosis factor-$\alpha$ (TNF-$\alpha$).

A new class of agents under investigation are the biologic TNF inhibitors, which include soluble TNF receptors, recombinant TNF receptors and anti-TNF monoclonal antibodies. These agents inhibit the action of TNF, a pro-inflammatory cytokine. TNF is responsible for much of the inflammation and joint destruction in rheumatoid arthritis, both directly, by inducing inflammation, and indirectly, by mediating the cascade of other pro-inflammatory cytokines.

Specific examples of recombinant TNF receptors include recombinant human TNF receptor p55 Fc fusion protein (p55 TNFR:Fc) and recombinant human TNF receptor p75 Fc fusion protein (p75 TNFR:Fc), the latter being a dimeric form of the p75 TNF receptor created by fusion to the Fc fragment of human immunoglobulin IgG1. The p55 and p75 TNFR:Fc bind to soluble TNF present in the synovial fluid of a patient suffering from rheumatoid arthritis, thereby reducing its inflammatory action and resulting in a significant reduction in joint tenderness and swelling.

The above-mentioned drug treatments are typically administered to patients after the onset of rheumatoid arthritis, and may slow progression of the disease and provide some degree of relief from the symptoms associated with the disease. However, these drug treatments fail to address the underlying cause of rheumatoid arthritis which, as with autoimmune and alloimmune diseases in general, is an inappropriate immune response. Therefore, once these treatments are discontinued, the symptoms of rheumatoid arthritis typically re-appear. This is also true of other current drug treatments for other autoimmune and alloimmune disorders.

The use of drug treatments on a long-term basis can be costly and may have undesirable side effects and should therefore be avoided. Consequently, the need exists for alternate treatments which avoid the long-term use of drugs while providing long-term relief from symptoms of auto immune and alloimmune diseases such as rheumatoid arthritis.

SUMMARY OF THE INVENTION

The present invention provides a novel method of treating autoimmune and alloimmune diseases which provides advantages over previously known treatments, such as those discussed above for the treatment of rheumatoid arthritis.

The method of treatment according to the invention comprises a combination therapy for administration to a subject after the onset of an autoimmune or alloimmune disease in that subject. One component of the therapy comprises administration of a drug treatment to bring about at least a partial remission of the disease and/or one or more of the symptoms associated with the disease. Preferably, the drug treatment is one which does not have an effect on the underlying immune response of the subject but, as with the biologic TNF inhibitors mentioned above, blocks the effector stage of the immune response.

The other component of the combination therapy comprises administering to the subject autologous mammalian blood which has been modified extracorporeally by exposure to at least one stressor selected from the group consisting of an oxidative environment, an electromagnetic emission and a temperature above or below body temperature.

Mammalian blood modified in this manner has been shown to be effective for preventing the onset of autoimmune diseases. In this regard, see U.S. Pat. No. 5,980,954 to Bolton, issued on Nov. 9, 1999, entitled "Treatment of Autoimmune Diseases", which is incorporated herein in its entirety.

A possible mechanism by which modified mammalian blood alleviates autoimmune and alloimmune diseases is discussed in detail in above-mentioned U.S. Pat. No. 5,980,954. This mechanism involves T-cells, a type of lymphocyte which play a significant role in the control of the immune system. T-cells include CD-8 cells, and CD-4 cells otherwise known as T-helper cells that are further subdividable into TH1 and TH2 cells. TH1 cells secrete pro-inflammatory cytokines such as interferon gamma, which leads to the production of TNF-α. On the other hand, TH2 cells are considered to be regulatory cells and secrete regulatory cytokines, such as interleukins-4 and -10. In a normal, healthy individual, the ratio of TH1 cells to TH2 cells is about 3:1. In individuals suffering from an autoimmune or alloimmune condition, there is usually an imbalance in the TH cell types, often with an increase in the ratio of TH1 cells to TH2 cells, as in rheumatoid arthritis, which is believed to result in inflammatory conditions often noted in autoinimune diseases such as rheumatoid arthritis. It is believed that a number of components of modified autologous mammalian blood, upon re-injection into the patient, upregulate the proportion of TH2 cells in a patient's blood, thereby increasing the secretion of regulatory cytokines and preventing the secretion of abnormal amounts of pro-inflammatory cytokines and the consequent appearance of symptoms such as inflammation commonly associated with autoimmune and alloimmune diseases.

Therefore, the present invention provides a combination therapy for autoimmune and alloimmune diseases in which remission of the disease is reduced with certain drug therapies, and administration of modified autologous mammalian blood is used to maintain remission of the disease. The combination therapy provides a safe and effective treatment of autoimmune and alloimnune diseases such as rheumatoid arthritis while avoiding the long-term use of drugs to treat symptoms of the disease, potentially providing a substantial cost saving and reduced incidence of significant adverse side effects caused by the continued use of drug therapies.

BRIEF DESCRIPTION OF THE DRAWINGS

The invention will now be described, by way of example only, with reference to the following drawings, in which:

FIG. 1 is a graphical representation of the results of Example 2 described below.

DETAILED DESCRIPTION OF PREFERRED EMBODIMENTS

The following discussion of preferred embodiments of the invention relates to preferred combination therapies according to the invention for the treatment of rheumatoid arthritis. However, the combination therapy according to the invention is expected to be useful in the treatment of a number of other autoimmune and alloimmune diseases, including those specifically listed above, in combination with drug treatments which reduce symptoms and/or cause complete or total remission of these diseases.

In a particularly preferred embodiment, the combination therapy according to the invention is used in the treatment of mammalian subjects, preferably humans, suffering from rheumatoid arthritis. The therapy is preferably commenced after onset of the disease, at which time the subjects are exhibiting tenderness and swelling in a number of joints. More preferably, the therapy is commenced at the first onset of symptoms, before significant irreversible joint damage has occurred.

In order to alleviate joint tenderness and swelling, subjects are preferably treated with one or more TNF inhibitors which are effective to induce remission of rheumatoid arthritis by reducing TNF activity. Preferred TNF inhibitors are biologic TNF inhibitors selected from the group comprising soluble TNF receptors, recombinant TNF receptors and anti-TNF monoclonal antibodies. Preferred recombinant TNF receptors are selected from recombinant human TNF receptor p75 Fc fusion protein (p75 TNFR:Fc) and recombinant human TNF receptor p55 Fc fusion protein (p55 TNFR:Fc), with p75 TNFR:Fc being more preferred.

Other preferred biologic TNF inhibitors include fusion proteins consisting of the extracellular domains of the human p55 TNF-α receptor fused to the human IgG1heavy chain, anti-TNF-α monoclonal antibodies and (4-(3-cyclopentyloxy4-methoxyphenyl)-2-pyrrolidone), a type IV phosphodiesterase inhibitor which has recently been shown to down-regulate the production of TNF-α by lymphocytes and macrophages.

The most preferred TNF inhibitors for use in the present invention are p75 TNFR:Fc fusion protein and anti-TNF monoclonal antibodies.

The therapeutic agent is administered to the subject until joint tenderness and swelling has been partially or completely relieved. For example, p75 TNFR:Fc is administered via intravenous infusion, with several doses being administered over a period of about two to three weeks. In one particularly preferred embodiment, 10 mg/m$^2$ p75 TNFR:Fc is administered as a single IV infusion over 30 minutes on days 1 and 15 and 5 mg/m$^2$ on days 3, 5, 17 and 19. Patients are evaluated for response during weeks 7 and 11, and those patients with a minor response, partial response or complete response are given a second course of therapy beginning at about week 12. Preferably, a maximum of three such cycles of therapy are administered. After completion of the treatment with p75 TNFR:Fc, there is typically about a 50% reduction in the number of sore joints and a corresponding decrease in joint swelling.

After sufficient TNF inhibitor has been administered to partially or completely relieve joint swelling or tenderness, treatment with the TNF inhibitor is preferably discontinued and administration of modified autologous mammalian blood is commenced in order to maintain the remission of the symptoms achieved by treatment with the TNF inhibitor. In other preferred embodiments of the invention, the TNF inhibitor and modified mammalian blood are administered concurrently to a subject exhibiting joint tenderness and swelling brought about by rheumatoid arthritis. The administration of modified mammalian blood may be commenced before, during or after the commencement of the treatment with the TNF inhibitor. Once the symptoms have been brought into remission, administration of the TNF inhibitor is preferably discontinued and the treatment with modified mammalian blood may be continued as required. Periodic treatments with modified mammalian blood, for an indefinite period of time, may be preferred to prevent reappearance of disease symptoms.

By using the combination therapy according to the invention, continuous, long-term administration of therapeutic agents such as p 75 TNFR:Fc can be avoided, thereby significantly reducing expense as well as the chance that subjects will experience significant adverse side effects.

The following is a description of preferred methods for modifying mammalian blood for use in the combination therapy according to the invention.

In a preferred process of the present invention, an aliquot of blood is extracted from a mammalian subject, preferably a human, and the aliquot of blood is treated ex vivo with certain stressors, described in more detail below. The terms "aliquot", "aliquot of blood" or similar terms used herein include whole blood, separated cellular fractions of the blood including platelets, separated non-cellular fractions of the blood including plasma, plasma components, and combinations thereof. The effect of the stressors is to modify the blood, and/or the cellular or non-cellular fractions thereof contained in the aliquot. The modified aliquot is then re-introduced into the subject's body by any suitable method, most preferably intramuscular injection, but also including subcutaneous injection, intraperitoneal injection, intra-arterial injection, intravenous injection and oral, nasal or rectal administration.

The stressors to which the aliquot of blood is subjected ex vivo according to the method of the present invention are selected from temperature stress (blood temperature above or below body temperature), an oxidative environment and an electromagnetic emission, individually or in any combination, simultaneously or sequentially. Suitably, in human subjects, the aliquot has a sufficient volume, when re-introduced into the subject's body, to maintain the remission of one or more symptoms of the autoimmune or alloimmune disease. Preferably, the volume of the aliquot is up to about 400 ml, preferably from about 0.1 to about 100 ml, more preferably from about 5 to about 15 ml, even more preferably from about 8 to about 12 ml, and most preferably about 10 ml.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and an electromagnetic emission, or an electromagnetic emission and oxidative stress. Care must be taken to utilize an appropriate level of the stressors to thereby effectively modify the blood to achieve the desired effect.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, the desired effect will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about −5° C. to about 36.5° C., even more preferably from about 10° C. to about 30° C., and even more preferably from about 15° C. to about 25° C.

The oxidative environment stressor can be the application to the aliquot of solid, liquid or gaseous oxidizing agents. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the therapy is rendered ineffective. Suitably, the gas stream has an ozone content of up to about 300 µg/ml, preferably up to about 100 µg/ml, more preferably about 30 µg/ml, even more preferably up to about 20 µg/ml, particularly preferably from about 10 µg/ml to about 20 µ/ml, and most preferably about 14.5±1.0 µg/ml. The gas stream is suitably supplied to the aliquot at a rate of up to about 2.0 litres/min, preferably up to about 0.5 litres/min, more preferably up to about 0.4 litres/min, even more preferably up to about 0.33 litres/min, and most preferably about 0.24±0.024 litres/min. The lower limit of the flow rate of the gas stream is preferably not lower than 0.01 litres/min, more preferably not lower than 0.1 litres/min, and even more preferably not lower than 0.2 litres/min.

The electromagnetic emission stressor is suitably applied by irradiating the aliquot under treatment from a source of an electromagnetic emission while the aliquot is maintained at the aforementioned temperature and/or while the oxygen/ozone gaseous mixture is being bubbled through the aliquot. Preferred electromagnetic emissions are selected from photonic radiation, more preferably ultraviolet (UV), visible and infrared light, and even more preferably UV light. The most preferred sources of UV light are UV lamps emitting primarily UV-C band wavelengths, i.e. wavelengths shorter than about 280 nm. Such lamps may also emit amounts of visible and infrared light. Sources of UV light corresponding to standard UV-A (wavelengths from about 315 to about 400 nm) and UV-B (wavelengths from about 280 to about 315) can also be used. For example, an appropriate dosage of such UV light, applied simultaneously with one or both of the aforementioned temperature and oxidative environment stressors, can be obtained from up to eight lamps arranged to surround the sample container holding the aliquot, operated at an intensity to deliver a total UV light energy at the surface of the blood of from about 0.025 to about 10 joules/cm$^2$, preferably from about 0.1 to about 3.0 joules/cm$^2$. Preferably, four such lamps are used.

The time for which the aliquot is subjected to the stressors is normally within the time range of up to about 60 minutes. The time depends to some extent upon the chosen intensity of the electromagnetic emission, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting blood temperature, and the rate at which it can be warmed or cooled to a predetermined temperature, tends to vary from subject to subject. Such a treatment provides a modified blood aliquot which is ready for injection into the subject.

In one preferred embodiment of the present invention, the aliquot of blood is stressed by being simultaneously subjected to all three of the above stressors using an apparatus of the type described in U.S. Pat. No. 4,968,483, issued on Nov. 6, 1990 to Mueller. The aliquot is placed in a suitable, sterile, W light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

The invention is further illustrated and described with reference to the following specific examples, in which the beneficial effects of the present invention are demonstrated in vivo by clinical experiments on rats, specifically male Lewis rats in which rheumatoid-like arthritis has been induced. An animal model used for studying rheumatoid arthritis is adjuvant-induced arthritis in a rat model (see, for example, Pearson, C., 1956, "Development of Arthritis, periarthritis and periostitis in rats given adjuvant", *Proc. Soc. Exp. Biol. Med.*, 91:95). According to this model, arthritis is induced in rats by injecting them with adjuvant containing *Mycobacterium butyricum*.

EXAMPLE 1

This example describes the use of a TNF-α inhibitor to induce remission of rheumatoid arthritis.

An adjuvant mixture was prepared for induction of arthritis by suspending 50 mg *M. butyricum* (Difco Laboratories, Inc., Detroit, Mich.) in 5 ml light white paraffin oil—m3516 (Sigma Chemical Co., St. Louis, Mo.) and thoroughly mixed using a homogenizer.

Male Lewis rats, 6 to 8 weeks of age, were each injected subcutaneously, at the base of the tail, with an aliquot of the mixture sufficient to supply 0.15 mg *M. butyricum.* Symptoms of arthritis, as evidenced by limb swelling, appeared in each animal about 12 days after induction.

Treatment with p75 TNFR:Fc begins on the day of onset of clinical arthritis, i.e., on the first day of joint swelling. The treatment with P75 TNFR:Fc comprises injection of 1–5 mg/kg into the peritoneum. Animals in the control group are injected with saline or isotype control antibody.

Each animal is monitored for the severity and progression of the disease by measuring both foot volume and clinical score. Immunohistochemical analysis of joints is also carried out to confirm the remission and relapse of rheumatoid arthritis. To monitor the effectiveness of the TNF-α inhibition, a TNF-α-dependent cell line Wehi 1643 is used to measure the biological activity of TNF-α in both sera and synovial fluids.

The results of the study show that a short course of treatment with P75 TNFR:Fc inhibits progression and causes remission of the symptoms of rheumatoid arthritis, with decreased TNF-α activity being observed in animals treated with P75 TNFR:Fc. As expected, progression of the disease is observed shortly after termination of treatment with P75 TNFR:Fc.

EXAMPLE 2

This example demonstrates the effectiveness of the treatment with modified blood according to the invention to prevent the onset of rheumatoid arthritis.

Male Lewis rats, 4 to 5 weeks of age, 100 to 120 g, were obtained from Charles River Laboratories, quarantined one week and entered into the study. An adjuvant mixture was prepared as described above in Example 1 and aliquots of the mixture sufficient to supply 0.15 mg *M. butyricum* was injected into each animal subcutaneously, at the base of the tail. Symptoms of arthritis appeared about 12 days after induction, in each animal, as evidenced by limb swelling.

Blood was collected from donor animals, not injected with the adjuvant mixture, by cardiac puncture. 10 ml of citrated donor blood was transferred to a sterile, low density polyethylene vessel for ex vivo treatment with stressors according to the invention. Using an apparatus as described in the above-mentioned Mueller patent (more specifically, a VasoCare™ V7000 apparatus), the blood was heated to 42.5±1° C. and at that temperature irradiated with ultraviolet light, principally at a wavelength of 254 nm, while a gas mixture of medical grade oxygen containing 14.5±1.0 μg/ml of ozone was bubbled through the blood at a flow rate of 240±24 ml/min.

Six animals were given a course of 2 injections of 0.2 ml aliquots of the treated blood, on days 1 and 2 after disease induction. Eighteen animals were injected with untreated blood or saline as controls. Hind paw volumes and clinical scores of the animals were measured every 2 to 3 days for 5 weeks after disease induction. Hind paw volumes were measured by water displacement in a 250 ml beaker using a top-loaded Mettler balance.

The results of this study showed that the incidence of arthritis in the treated group was decreased as compared with the control group, as measured both by clinical scores and foot volumes. The results of the foot volume measurements for each group of animals were averaged and are presented graphically on the accompanying FIG. 1, a plot of mean foot volume against days after induction of arthritis. The upper curve is derived from the control group of animals, the lower curve from the animals which received the course of injections of treated blood. A significant decrease in the severity of the arthritis, as indicated by lower foot volumes, is apparent for the treated animals as compared to the animals of the control group.

EXAMPLE 3

This example demonstrates the effectiveness of the combination therapy according to the invention, comprising the administration of P75 TNFR:Fc to bring about remission of rheumatoid arthritis, followed by the administration of modified blood to maintain remission of the disease.

Twenty Lewis rats are injected with adjuvant containing 0.15 mg *M. butyricum*. The preparation and injection of the adjuvant is conducted in the manner described above in Example 1. Administration of P75 TNFR:Fc is started on the day of onset of the disease, with the dose and number of injections being as described in Example 1.

The results of the treatment with P75 TNFR:Fc are similar to those observed in Example 1. Specifically, P75 TNFR:Fc inhibits progression and causes remission of the symptoms of rheumatoid arthritis, with decreased TNF-α activity being observed in animals treated with P75 TNFR:Fc.

Following the treatment with P75 TNFR:Fc, the animals are evenly divided into 4 groups. The animals of groups 1, 2 and 3 are injected with modified blood prepared according to the present invention. The animals of group 4 are left untreated as controls.

During and following the treatment with the combination therapy as described above, each group of animals is monitored for progression and severity of the disease by measuring both foot volume and clinical score as described in Example 1. Joint sections are collected at various time points after the treatment with modified blood and stained with hematoxylin and eosin to confirm the effect of the modified blood treatment on preventing the relapse of rheumatoid arthritis. Appropriate statistical analysis is used to determine the significance of the effect of the individual treatments comprising the combination therapy.

The above examples demonstrate that treatment of subjects with modified mammalian blood can effectively prevent the onset of rheumatoid arthritis in mammals, and that a therapy comprising administration of a biologic TNF inhibitor in combination with administration of modified blood is effective to bring about remission and prevent re-appearance of the symptoms and/or the disease.

Although the preferred embodiments have dealt primarily with a combination therapy comprising administration of modified mammalian blood and administration of P75 TNFR:Fc, it will be appreciated that similar results may be attained through the use of other biologic TNF inhibitors, including those specifically referred to above. Furthermore, it will be appreciated that administration of modified mammalian blood in combination with other drugs having anti-TNF properties may also provide an effective combination therapy for rheumatoid arthritis. Examples of such drugs are type IV phosphodiesterase inhibitors, dexamethasone (sodium phosphate), pentoxifylline, fusidic acid (sodiun salt), pentamidine (isethionate) and R-phenylisopropyladenosine (R-PIA), all of which were found to reduce serum TNF concentrations when tested for their anti-TNF activities in an endotoxin-induced shock rat model.

Although the invention has been described in connection with certain preferred embodiments, it is to be appreciated that it is not limited thereto. Rather, the present invention includes all embodiments which may fall within the scope of the following claims.

What is claimed is:

1. A method for treating a mammalian subject suffering from an autoimmune or an alloimmune disease, the method comprising:

administering to said subject a therapeutic treatment which results in at least partial remission of one or more symptoms of the autoimmune or alloimmune disease;

terminating said therapeutic treatment; and subsequently administering to said subject autologous mammalian blood which has been modified extracorporeally by exposure to at least one stressor selected from the group consisting of an oxidative environment, an electromagnetic emission and a temperature above or below body temperature, said modified mammalian blood being administered to said subject in an amount sufficient to maintain the remission of said one or more symptoms of the autoimmune or alloimmune disease.

2. The method of claim 1, wherein said autoimmune or alloimmune disease is selected from the group consisting of rheumatoid arthritis, multiple sclerosis, systemic lupus erythromatosis (SLE), scleroderma, diabetes, inflammatory bowel disease, psoriasis, atherosclerosis, graft versus host disease and tissue transplant rejection.

3. The method of claim 2, wherein said autoimmune or alloimmune disease is rheumatoid arthritis and said symptoms include joint tenderness and swelling.

4. The method of claim 2, wherein said therapeutic treatment comprises administration to said subject of one or more biologic tumor necrosis factor (TNF) inhibitors.

5. The method of claim 4, wherein said biologic TNF inhibitors are selected from one or more members of the group consisting of recombinant TNF receptors and anti-TNF monoclonal antibodies.

6. The method of claim 5, wherein said recombinant TNF receptor is selected from the group consisting of recombinant human TNF receptor p55 Fc fusion protein (p55 TNFR:Fc) and recombinant human TNF receptor p75 Fc fusion protein (p75 TNFR:Fc).

7. The method of claim 6, wherein said recombinant TNF receptor is p75 TNFR:Fc.

8. The method of claim 1, wherein said mammalian blood is modified extracorporeally by exposure to an electromagnetic emission, an elevated temperature and an oxidative environment.

9. The method of claim 8, wherein said electromagnetic emission comprises ultraviolet light.

* * * * *